United States Patent
Govari

(10) Patent No.: US 11,389,078 B2
(45) Date of Patent: Jul. 19, 2022

(54) REDUCING CAPACITANCE EFFECTS IN ACTIVE CURRENT LOCATION (ACL)

(71) Applicant: Biosense Webster (Israel) Ltd., Yokneam (IL)

(72) Inventor: Assaf Govari, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 366 days.

(21) Appl. No.: 16/059,401

(22) Filed: Aug. 9, 2018

(65) Prior Publication Data

US 2020/0046251 A1    Feb. 13, 2020

(51) Int. Cl.
| | |
|---|---|
| *A61B 5/06* | (2006.01) |
| *A61B 34/20* | (2016.01) |
| *A61B 5/0536* | (2021.01) |
| *A61B 5/0538* | (2021.01) |

(52) U.S. Cl.
CPC ............ *A61B 5/063* (2013.01); *A61B 5/0536* (2013.01); *A61B 5/0538* (2013.01); *A61B 34/20* (2016.02); *A61B 2034/2046* (2016.02)

(58) Field of Classification Search
CPC ..... A61B 5/0538; A61B 5/0536; A61B 5/068; A61B 5/065; A61B 5/063; A61B 5/061; A61B 2034/2051; A61B 2034/2046; A61B 34/20; A61B 5/287; A61B 2018/1467; A61B 2018/00577; A61B 2018/00595; A61B 2018/00351; A61B 18/1492; A61B 18/12
See application file for complete search history.

(56) References Cited

U.S. PATENT DOCUMENTS

| | | |
|---|---|---|
| 6,532,384 B1 | 3/2003 | Fukuda |
| 7,756,576 B2 | 7/2010 | Levin |
| 7,848,787 B2 | 12/2010 | Osadchy |
| 7,869,865 B2 | 1/2011 | Govari et al. |
| 8,456,182 B2 | 6/2013 | Bar-Tal et al. |
| 2006/0085049 A1 | 4/2006 | Cory et al. |
| 2007/0038078 A1 | 2/2007 | Osadchy |
| 2007/0060832 A1 | 3/2007 | Levin |
| 2011/0306867 A1 | 12/2011 | Gopinathan |
| 2017/0209066 A1 | 7/2017 | Chetham et al. |
| 2020/0000368 A1* | 1/2020 | Ben-Haim ........... A61B 5/0538 |

OTHER PUBLICATIONS

Extended European search report for corresponding European patent application No. EP 19190796.3, dated Dec. 2, 2019.

* cited by examiner

*Primary Examiner* — Tse W Chen
*Assistant Examiner* — Avery M Foley
(74) *Attorney, Agent, or Firm* — Notaro, Michalos & Zaccaria P.C.

(57) ABSTRACT

A method for location tracking, includes measuring one or more first impedance-magnitudes, between a probe located at a location in an organ of a patient and one or more body-surface electrodes, at a first electrical frequency. One or more second impedance-magnitudes, between the probe located at the location and the one or more body-surface electrodes, are measured at a second electrical frequency. Based on the measured first and second impedance-magnitudes, one or more probe zero-frequency impedance-magnitudes between the probe and the one or more body-surface electrodes are estimated. The location of the probe in the organ is estimated based on the one or more probe zero-frequency impedance-magnitudes.

4 Claims, 3 Drawing Sheets

REDUCING CAPACITANCE EFFECTS IN ACTIVE CURRENT LOCATION (ACL)

FIELD OF THE INVENTION

The present invention relates generally to tracking a probe location within a living body, and specifically to electrical catheter-based position measurements.

BACKGROUND OF THE INVENTION

Spatial mapping of an intrabody cavity is required in many medical procedures. For example, U.S. Patent Application Publication 2011/0306867 describes methods and systems for determining information about a vascular bodily lumen. An exemplary method includes generating an electrical signal, delivering the electrical signal to a plurality of excitation elements in the vicinity of the vascular bodily lumen, measuring a responsive electrical signal from a plurality of sensing elements in response to the delivered electrical signal, and determining a lumen dimension. Specific embodiments include generating a multiple frequency electrical signal. Another embodiment includes measuring a plurality of responsive signals at a plurality of frequencies. Still other embodiments include using spatial diversity of the excitation elements. Yet other embodiments use method for calibration and de-embedding of such measurements to determine the lumen dimensions. Diagnostic devices incorporating the method are also disclosed, including guide wires, catheters and implants.

U.S. Patent Application Publication 2006/0085049 describes systems and methods for discriminating and locating tissues within a body, which involve applying a waveform signal to tissue between two electrodes and measuring the electrical characteristics of the signal transmitted through the tissue. At least one of the electrodes is constrained in area so that localized electrical characteristics of the tissue are measured. Such localized electrical characteristics are determined over a portion of a body of the subject by using an array of electrodes or electrodes that can be moved over the body. A controller may implement the process and perform calculations on the measured data to identify tissue types and locations within the measured area, and to present results in graphical form. Results may be combined with other tissue imaging technologies and with image-guided systems.

SUMMARY OF THE INVENTION

An embodiment of the present invention provides a method for location tracking including measuring one or more first impedance-magnitudes, between a probe located at a location in an organ of a patient and one or more body-surface electrodes, at a first electrical frequency. One or more second impedance-magnitudes, between the probe located at the location and the one or more body-surface electrodes, are measured at a second electrical frequency. Based on the measured first and second impedance-magnitudes, one or more probe zero-frequency impedance-magnitudes between the probe and the one or more body-surface electrodes are estimated. The location of the probe in the organ is estimated based on the one or more probe zero-frequency impedance-magnitudes.

In some embodiments, the method further includes, prior to inserting the probe, acquiring using a calibration tool a set of calibration impedance-magnitudes at the first and second electrical frequencies, between the calibration tool located at calibration locations and the one or more body-surface electrodes, and acquiring corresponding calibration locations. Based on the acquired calibration impedance-magnitudes, one or more calibration zero-frequency impedance-magnitudes between the calibration tool and the one or more body-surface electrodes are estimated. Estimating the location of the probe includes comparing the probe zero-frequency impedance-magnitudes to the calibration zero-frequency impedance-magnitudes.

In some embodiments, the method includes interpolating the calibration zero-frequency impedance-magnitudes, so as to produce one or more interpolated zero-frequency calibration impedance-magnitudes that best match the one or more probe zero-frequency impedance-magnitudes.

In an embodiment, the method includes reducing a capacitive distortion in the first and second impedance-magnitudes that were measured at the first and second electrical frequencies.

In another embodiment, the capacitive distortion is caused by at least another probe located in the organ.

There is additionally provided, in accordance with an embodiment of the present invention, a location tracking system, including a memory and a a processor. The memory is configured to store (i) one or more first impedance-magnitudes, measured at a first electrical frequency between a probe located at a location in an organ of a patient and one or more body-surface electrodes, and (ii) one or more second impedance-magnitudes, measured at a second electrical frequency between the probe located at the location and the one or more body-surface electrodes. The processor is configured to, based on the measured first and second impedance-magnitudes, estimate one or more probe zero-frequency impedance-magnitudes between the probe and the one or more body-surface electrodes, estimate the location of the probe in the organ based on the one or more probe zero-frequency impedance-magnitudes.

The present invention will be more fully understood from the following detailed description of the embodiments thereof, taken together with the drawings in which:

DETAILED DESCRIPTION OF EMBODIMENTS

Overview

Figure 1:
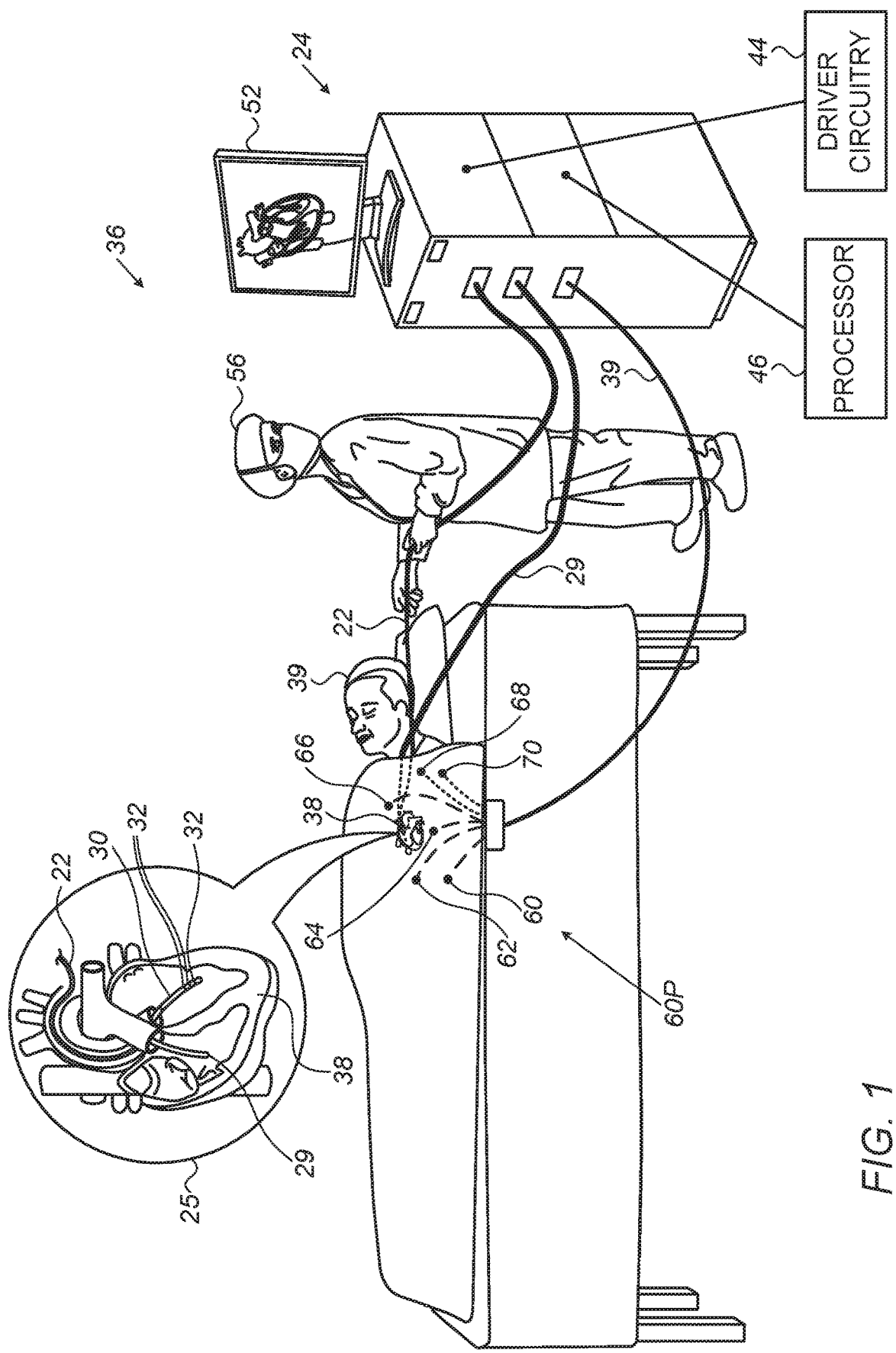
FIG. 1 is a schematic, pictorial illustration of a zero-frequency impedance-based Active Current Location (ACL) tracking system, in accordance with an embodiment of the present invention.

Embodiments of the present invention that are described hereinafter provide an impedance-based catheter location-tracking system, and a method capable of tracking a location of a probe in an organ despite deviations in impedance-magnitude values. Deviating impedance-magnitude values may occur, for example, when several probes are present in an organ in parallel, which adds a capacitive impedance in parallel. The measured impedance-magnitude values then deviate relative to location-calibrated impedance-magnitude values, as described below.

The disclosed system is capable of retracing the deviating impedance-magnitudes to location-calibrated impedance-magnitudes, so as to accurately determine locations of one or more probes. To achieve this goal, the system initially measures the impedance-magnitudes at two or more different electrical frequencies at each probe location, rather than at a single electrical frequency, as further described below.

An example of an impedance-based catheter location-tracking system is the Carto® 3 system (made by Biosense-Webster, Irvine, Calif.), which applies an Active Current Location (ACL) impedance-based position-tracking method. With the ACL method, a processor receives position-indicative impedance-magnitudes that are measured between an electrode fitted at a distal end of a catheter and surface electrodes attached to the patient's skin. Based both on the measured impedance-magnitudes and on a stored location-calibrated impedance-magnitudes, the processor of the Carto® 3 system estimates a location of the catheter inside an organ of a patient.

The location-calibration of impedance-magnitudes is performed using another, more accurate, location tracking method, such as one based on magnetic signals or on imaging. During such calibration, the location-tracking system (a) measures a set of coordinates of intrabody locations; (b) measures respective impedance-magnitudes at the respective locations using a calibration tool; (c) calibrates the measured impedance-magnitudes by deriving a relation that connects each measured coordinate with a corresponding measured impedance-magnitude (i.e., correlates the measured impedance-magnitude with the respective coordinate), and; (d) saves the calibration impedance-magnitudes and the respective location coordinates (also termed hereinafter "calibration location") in a memory. In some embodiments the location-tracking system applies the calibration tool to perform step (a), using for example a magnetic position sensor that is fitted at a distal end of the calibration tool.

Subsequently, e.g., during an investigative session, a processor tracks the location of a probe by correlating impedance-magnitudes measured by the probe (named hereinafter "probe impedance-magnitudes") with the stored calibration impedance-magnitudes (i.e., using the ACL method) and estimates the corresponding coordinates of the unknown location based on the stored set of coordinates.

In some cases, however, the legacy ACL method may encounter difficulties, such as when several probes are inserted into the heart in parallel. The simultaneous presence of several probes changes the electrical conditions that each probe experiences relative to those experienced by the calibration tool. Specifically, the insertion of several probes may add capacitive impedance in parallel. As a result, impedance-magnitudes measured by any of the probes will generally deviate to lower values than those measured by the calibration tool during calibration. In such a case, the correct location of any of the probes can no longer be estimated by comparing the (deviating) impedance-magnitudes with the calibrated impedance-magnitudes.

To track a location using deviating impedance-magnitudes, embodiments of the present invention estimate and utilize the Ohmic component of the impedance (also named "DC impedance" or "zero-frequency impedance"). The zero-frequency impedance is unaffected by the presence of parallel capacitive impedances since any parallel capacitive component of an impedance will diminish (i.e., becomes an open-circuit) at zero-frequency. Therefore, in embodiments of the present invention, a processor correlates a zero-frequency probe-impedance $Z_{PT}(0)$ with stored zero-frequency calibration-impedances $Z_{Cal}(0)$ to correctly estimate a location of a probe. The disclosed method is named hereinafter "zero-frequency ACL."

As noted above, in order to derive the zero-frequency impedance, two different calibration impedance-magnitudes are measured during the calibration phase: one at a first electrical frequency and another at a second electrical frequency. Using the dual frequency measurements, a processor derives a location-calibrated zero-frequency impedance, $Z_{Cal}(0)$, e.g., by extrapolating the frequency-dependence of the impedance-magnitude to DC. Subsequently, during a probe tracking phase, probe impedance-magnitudes are also measured at the first electrical frequency and at the second electrical frequency. Using these measurements, the processor derives the probe zero-frequency impedance, $Z_{PT}(0)$, as further described below.

In an embodiment, the processor interpolates over zero-frequency calibration-impedances to find interpolated values that best match the zero-frequency probe-impedances. Next, based on interpolating over respective measured locations, the processor estimates a respective interpolated location of the probe. In an optional embodiment, the calibrated impedance-magnitudes and the probe impedance-magnitudes are measured at one or more additional frequencies (e.g., at a third frequency), so as to derive respective zero-frequency impedances with, for example, improved accuracy.

Using the disclosed zero-frequency ACL impedance-based location-tracking method and system, a processor is capable of correctly estimating the location of a probe in an organ, despite the presence of capacitive effects that distort the measurement. This technique is useful, for example, in procedures in which multiple probes are present in the patient organ simultaneously. As another example, the technique is useful in mitigating group coupling between cable patches (e.g., between cables carrying high voltages and cables carrying low voltages). The disclosed technique enables tracking of multiple probes without requiring additional location tracking techniques. This advantage may simplify multi-probe-based investigative and therapeutic systems and procedures, such as those used in cardiac catheterization.

System Description

FIG. 1 is a schematic, pictorial illustration of a zero-frequency impedance-based Active Current Location (ACL) location sensing system 36, in accordance with an embodiment of the present invention. ACL system 36 is used in determining the location of a probe distal end 30, which is fitted at the distal end of a shaft 22, as seen in inset 25. Distal end 30 is inserted by a physician 56 into an organ, such as a heart 38 of a patient 39.

Typically, distal end 30 of the probe is configured to perform diagnostics, such as mapping electrical potentials in the heart to identify locations where an arrhythmia may originate, or through which it may propagate. For such purposes, distal end 30 comprises multiple distal-electrodes 32. Distal-electrodes 32 are connected by wires through shaft 22 to driver circuitry 44 connected to a processor 46 that is included in a console 24, whereas driver circuitry 44 drives distal-electrodes 32 as commanded by processor 46.

As seen in inset 25, an additional probe 29 is present in heart 38, which causes impedance-magnitudes measured using electrodes 32 to deviate, e.g., to be lower than those measured at a same location during calibration phase. As noted above, the lower impedance-magnitudes (sensed using electrodes 32) will indicate wrong locations for electrodes 32 if not retraced to zero-frequency impedances by the disclosed zero-frequency ACL method.

Six body-surface electrodes, for receiving signals, are attached to the skin of the patient, which are named hereinafter ACL patches 60, 62, 64, 66, 68, and 70, or collectively named hereinafter "ACL patches 60P". As seen, ACL patches 60P are placed at the chest and back around heart 38 of patient 39. The signals for deriving impedance-magnitudes are passed to a driver circuitry 44, which is connected to ACL patches 60P by wires through cable 39. In some embodiments, driver circuitry 44 is configured to generate signals (i.e., currents and/or voltages) at two or more different electrical frequencies. Distal-electrodes 32 are configured to be driven by these signals, at the two or more different electrical frequencies. ACL patches 60P are configured to receive the resulting signals. The signals at the two or more frequencies may be applied and measured simultaneously or separately, using multiplexing and demultiplexing techniques known in the art.

In an embodiment, each of the six ACL patches 60P is used for measuring impedance-magnitudes to distal-electrodes 32. The measured impedance-magnitudes are indicative of locations of the one or more distal-electrodes 32. In the absence of any additional probe 29, processor 46 estimates the locations of each of the electrodes 32 inside heart 38 based on a stored set of calibration impedance-magnitudes and the measured respective locations (namely the ACL method). Driver circuitry 44 drives a display 52, which may show the locations of each of distal electrodes 32 inside heart 38.

With the presence of additional probe 29, the measured impedance-magnitudes deviate, and are typically lower than those calibrated. Still, using the disclosed zero-frequency ACL method for deriving zero-frequency impedances from deviating impedances, and based on a stored set of zero-frequency calibration impedance-magnitudes, processor 46 correctly estimates the locations of each of distal electrodes 32 inside heart 38, as described below.

The method of electrode location sensing using ACL system 36 in conjunction with calibrated impedances is implemented in various medical applications, for example, in some CARTO™ systems produced by Biosense-Webster described in detail in U.S. Pat. Nos. 7,756,576, 7,869,865, 7,848,787, and 8,456,182 whose disclosures are all incorporated herein by reference. The number of ACL patches can be larger than six, whereas using six ACL patches is described by way of example.

Processor 46 is typically a general-purpose computer, with suitable front end, interface circuits for receiving signals from ACL patches 60P and/or distal-electrodes 32, and appropriate signal processing circuits. Processor 46 is programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

Typically, system 36 includes other elements, which are not shown in the figures for the sake of simplicity, and which are referred to as necessary in the following description. For example, system 36 may include an ECG monitor, coupled to receive signals from one or more body surface ECG electrodes, so as to provide an ECG synchronization signal to console 24. As another example, system 36 may comprise one or more additional catheters, such as an ablation catheter and/or additional sensing-catheter, which, as noted, are not shown for clarity.

System 36 shown in FIG. 1 is an example chosen purely for the sake of conceptual clarity. In alternative embodiments, the impedance-magnitudes can be derived by, for example, a location-tracking system that applies voltage gradients between pair of patches 60P and measures, using electrodes 32, voltages induced at heart 38 (e.g., by using, for example, the Carto® 4 system produced by Biosense-Webster). In general, embodiments of the present invention may apply to any catheter-based location sensing method that uses modulated electrical signals which are position-indicative.

Additional types of catheters or other intrabody devices may be used in parallel for other purposes, by themselves or in conjunction with treatment devices such as a radiofrequency ablating-catheter.

Location sensing system 36 may be used in other organs with probes similar to probe 30.

Reducing Capacitance Effects in ACL

Figure 2A:
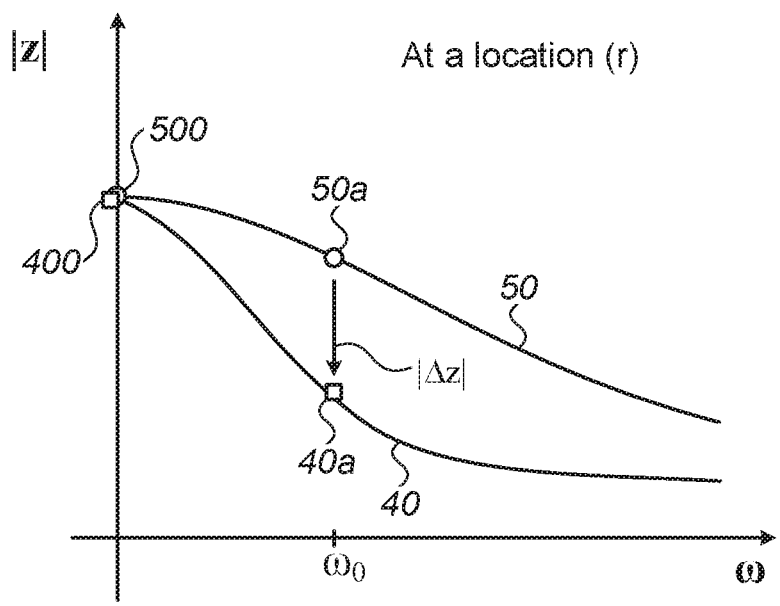
FIGS. 2A and 2B are schematic, pictorial illustrations of a zero-frequency ACL method, in accordance with an embodiment of the present invention.
Figure 2B:
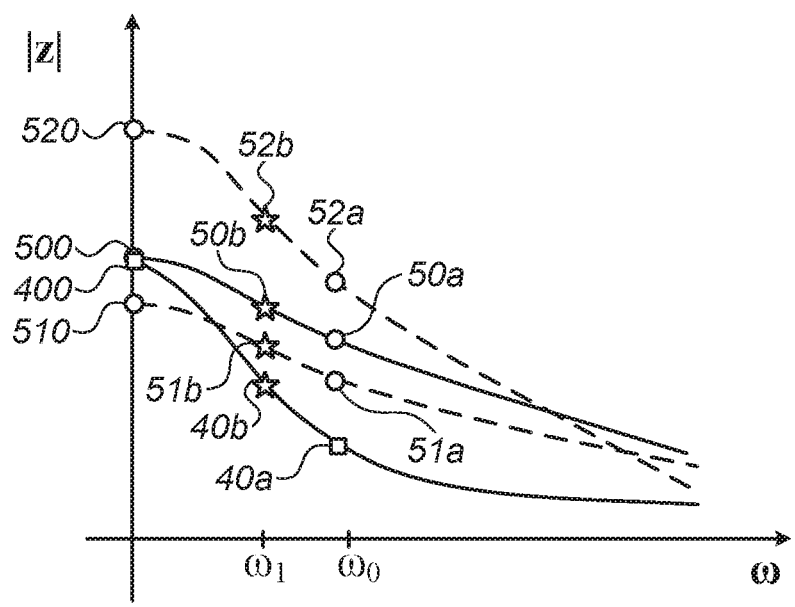

FIGS. 2A and 2B are schematic, pictorial illustrations of the zero-frequency ACL method, in accordance with an embodiment of the present invention. For simplicity, the figures refer to a single zero-frequency component of a single impedance-magnitude curve. In practice, one or more first impedance-magnitudes are measured at a first electrical frequency and respectively at a second electrical frequency (e.g., for each of axes x, y, and z). The one or more impedance-magnitudes are measured between one or more distal electrodes 32 of while the probe is located at a location in an organ and one or more body-surface electrodes 60P. Next, based on the measured first and second impedance-magnitudes, processor 46 estimates one or more zero-frequency impedances between the probe and the one or more body-surface electrodes. Finally, the processor estimates the location of the probe in the organ based on the one or more zero-frequency impedances, for example, by correlating the one or more zero-frequency impedances with a stored set of location-calibrated zero-frequency impedances, one by one.

FIG. 2A shows a probe impedance-magnitude 40a measured using electrode 32 at distal end 30 at an unknown location in heart 38, at an electrical frequency $\omega_0$, $|Z_{PT}(\omega_0)|$. The measured impedance-magnitude is typically lower than one measured by a calibration tool at the same location during calibration, 50a (i.e., $|Z_{Cal}(\omega_0)|$), due to the presence of other probes in the heart. The shown difference $|\Delta Z|$ is not known and therefore there is no way to retrace probe impedance-magnitude 40a to calibration impedance-magnitude 50a from a measurement at a single electrical frequency.

As seen, impedance-magnitude 40a (i.e., $|Z_{PT}(\omega_0)|$) lays on a frequency-dependent tissue bio-impedance-magnitude curve 40 of $|Z_{PT}(\omega)|$. Generally, tissue impedance-magnitude curve $|Z(\omega)|$ can be presented schematically using an equivalent electrical circuit made of a resistance $R_1$ connected in parallel to a resistance $R_2$ in series with a capacitance C:

$$|Z(\omega)| = R_1 \frac{\sqrt{1 + (\omega R_2 C)^2}}{\sqrt{1 + [\omega(R_1 + R_2)C]^2}} \quad \text{Eq. 1}$$

At zero-frequency and at infinite frequency, $|Z(\omega)|$ is independent of the capacitance C and equals $R_1$ and $R_1R_2/(R_1+R_2)$, respectively. Empirically, an impedance-magnitude $|Z(\omega)|$ of a cardiac tissue decreases from approximately 300Ω at zero-frequency to approximately 100Ω at infinite frequency. A corresponding simplified representation of the bio-impedance-magnitude can therefore be given by, for example:

$$|Z(\omega)| = R\frac{\sqrt{1+(\omega RC)^2}}{1+(\alpha\omega RC)^2} \qquad \text{Eq. 2}$$

where R is the ohmic component and ωC is the capacitive component of the bio-impedance, and α may be determined empirically to be, for the above values of 300Ω and 100 Ω, α=3. According to Eq. 2, $|Z(\omega)|$ is a monotonic decreasing function of the capacitance C. Thus, for any final frequency ω>0, an increase in capacitance of a bio-environment, for example by inserting more probes, lowers $|Z(\omega)|$ by certain value $|\Delta Z|$. With regard to FIG. 2A, as noted above, the challenge is to retrace, from the deviating probe impedance-magnitude, values that a processor can reliably correlate with location-calibrated impedance-magnitudes.

FIG. 2A shows a zero-frequency probe impedance 400 and a zero-frequency calibration impedance 500 derived for a same location r in heart 38. As seen, the two impedances are equal despite curve 40 deviating from curve 50 over ω>0. Embodiments of the present invention utilize the fact that the zero-frequency impedance, R=Z(0), described above, does not change when a parallel capacitance is introduced, for example, by the presence of several probes. Z(0) is thus a repeatable characteristic of a given unknown location r in the heart, which the tracking system derives during calibration, and subsequently, during a probe tracking session.

FIG. 2B exemplifies several possible values of derived zero-frequency location-calibrated impedances 500, 510, and 520, which correspond to three different coordinates in heart 38. Zero-frequency probe-impedance 400 derived for the unknown location may correlate, by way of example, with one of zero-frequency impedances 500, 510, and 520, as further described below.

Zero-frequency impedances 500, 510, and 520 are derived from Eq. 2 by a processor, during a calibration phase, by substituting impedances measured at two different frequencies, $\omega_0$ and $\omega_1$, seen over respective impedance curves 50, 51, and 52, and solving a set of two equations with two variables (while the global parameter a is determined empirically).

As noted above, the processor concludes that the coordinate of the probe location is the same as a location coordinate that corresponds to zero-frequency calibration-impedance 500. The processor then readily identifies, and assigns to the unknown location r, a correct coordinate stored with zero-frequency calibration-impedance 500.

In an optional embodiment, the calibrated impedances and the probe impedances are measured at one or more additional frequencies (e.g., at a third frequency), to solve Eq. 2 without determining an a priori value for α. Either way, a processor calculates a corresponding curve $|Z(\omega)|$ (solving Eq. 2) and afterwards derives the zero-frequency impedance value by substituting ω=0 in Eq. 2.

The examples shown in FIGS. 2A and 2B are chosen purely for the sake of conceptual clarity. Additional or alternative calculation steps may be done. For example, in an optional embodiment, the processor calculates one or more interpolated zero-frequency calibration-impedances $Z_{Cal}^{+}(0)$ that best match zero-frequency probe-impedances $Z_{PT}(0)$ so as to assign, to an unknown location r, a correct interpolated respective location.

Figure 3:
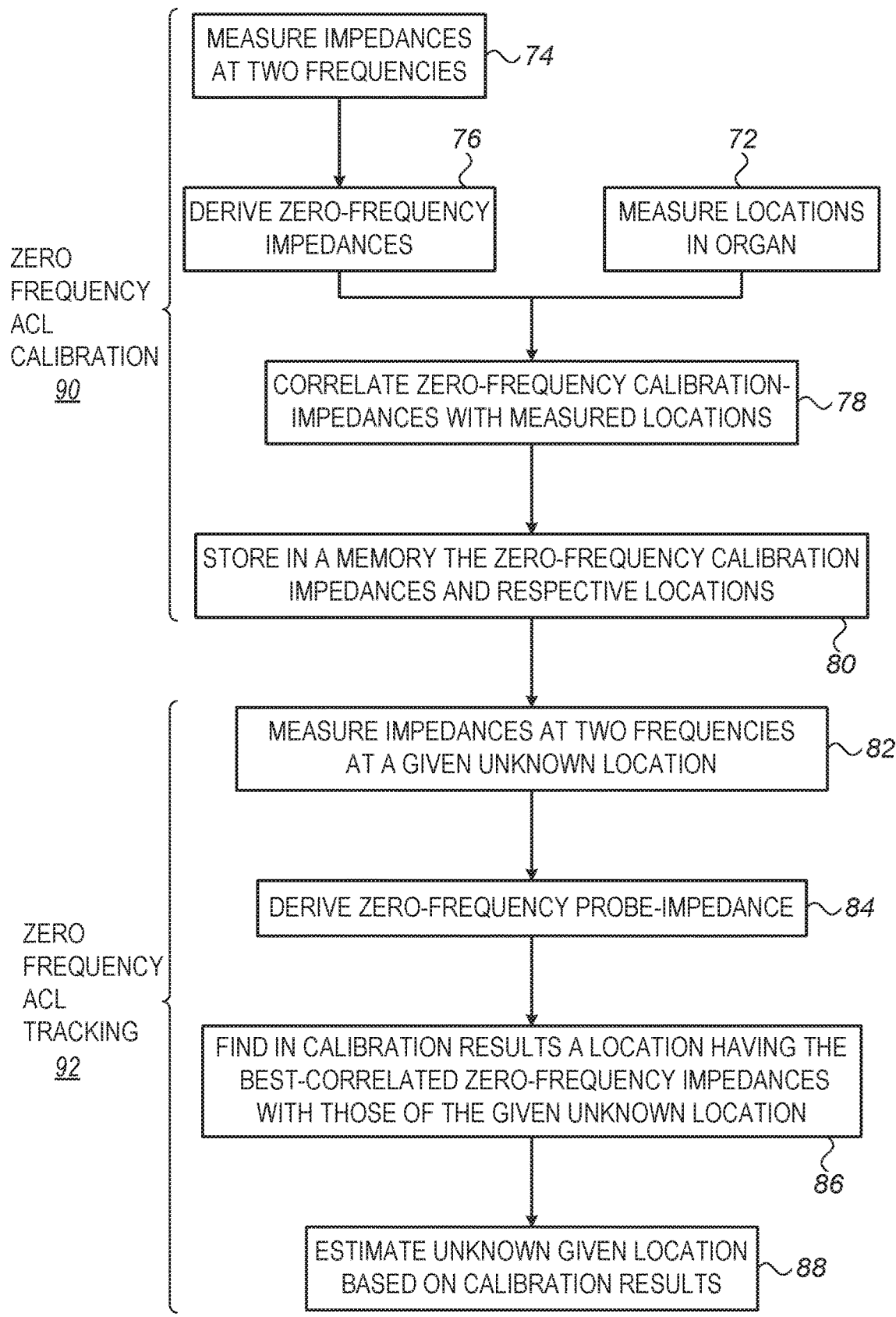
FIG. 3 is a flow chart schematically illustrating the zero-frequency ACL method for estimating a location of a probe, in accordance with an embodiment of the present invention.

FIG. 3 is a flow chart schematically illustrating the zero-frequency ACL method for estimating a location of a probe, in accordance with an embodiment of the present invention. The process begins with a zero-frequency ACL calibration phase 90, after which the system is operated in a zero-frequency ACL tracking phase 92.

In some embodiments, prior to inserting the probe for performing a tracking, a calibration tool is inserted and acquires a set of calibration zero-frequency impedance-magnitudes between the calibration tool, while being located at calibration locations, and the one or more body-surface electrodes 60P at the first and second electrical frequencies, and corresponding calibration locations;

Processor 46 estimates, based on the acquired first and second impedance-magnitudes, one or more zero-frequency impedance-magnitudes between the calibration tool and the one or more body-surface electrodes.

In calibration phase 90 processor 46 correlates between a set of zero-frequency impedances $\{Z_{Cal}(0)\}_{Locations}$ and a respective set of locations of in heart 38 (i.e., by deriving zero-frequency calibration-impedances at respective measured locations).

Calibration phase 90 begins with position tracking system 36 accurately measuring a location in heart 38, at a location measurement step 72. In parallel, system 36 measures, at the location, respective calibration impedance-magnitudes at two frequencies, at an impedances acquisition step 74. Based on the calibration impedance-magnitudes, processor 46 derives the multiple respective zero-frequency calibration-impedances $\{Z_{Cal}(0)\}$, at an impedance derivation step 76. Next, processor 46 correlates the derived multiple zero-frequency calibration-impedances with the respective location, at an impedance calibration step 78. At a storing step 80, processor 46 stores in a memory the multiple zero-frequency calibration-impedances with the corresponding coordinates of measured locations. The process repeats itself over the various calibrated locations, until a portion of heart 38 is location-calibrated.

During tracking phase 92, several probes are present in the organ and hence lower the impedances measured by probe 30. The lowered (i.e., deviating) impedances are again measured at two frequencies, at a probe impedance-magnitude measurement step 82. Next, processor 46 derives, from the measured probe impedance-magnitudes, zero-frequency probe-impedances, $\{Z_{PT}(0)\}$, at a derivation step 84. Next, processor 46 finds in calibration results a location having the best-correlated zero-frequency impedances with those of the given unknown location, at a location retrieval step 86. For that, processor 46 correlates the zero-frequency probe-impedances with the zero-frequency calibration-impedances that were stored in a memory at step 80, to find zero-frequency calibration-impedances, $\{Z_{Cal}^{*}(0)\}$, $\{Z_{Cal}^{*}(0)\} \subseteq \{Z_{Cal}(0)\}_{Locations}$ that are best correlated with $\{Z_{PT}(0)\}$, i.e., having $Z_{Cal}^{*}(0) \approx Z_{PT}(0)$ for each component of the set $\{Z_{PT}(0)\}$, and then retrieving the measured location that corresponds to $\{Z_{Cal}^{*}(0)\}$. Finally, processor 46 estimates the unknown given based on the calibration results, at a location indicating step 88. In an embodiment, $\{Z_{Cal}^{*}(0)\}$ is a result of interpolation between values included in the set $\{Z_{Cal}(0)\}_{Locations}$, and processor 46 calculates a corresponding interpolated location between the measured locations. In an optional embodiment, processor 46 indicates the location of probe 30 that was estimated at step 88 on display 52.

The example flow chart shown in FIG. 3 is chosen purely for the sake of conceptual clarity. For example, the acquisition of signals during tracking and their analysis can be performed at least partially in parallel.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A location tracking method, comprising:
measuring one or more first impedance-magnitudes, between a probe located at a location in an organ of a patient and one or more body-surface electrodes, at a first electrical frequency;
measuring one or more second impedance-magnitudes, between the probe located at the location and the one or more body-surface electrodes, at a second electrical frequency;
estimating, based on the measured first and second impedance-magnitudes, one or more probe zero-frequency impedance-magnitudes between the probe and the one or more body-surface electrodes; and
estimating the location of the probe in the organ based on the one or more probe zero-frequency impedance-magnitudes,
prior to inserting the probe, acquiring using a calibration tool a set of calibration impedance-magnitudes at the first and second electrical frequencies, between the calibration tool located at calibration locations and the one or more body-surface electrodes, and acquiring corresponding calibration locations;
estimating, based on the acquired calibration impedance-magnitudes, one or more calibration zero-frequency impedance-magnitudes between the calibration tool and the one or more body-surface electrodes; and
wherein the estimating the location of the probe comprises comparing the probe zero-frequency impedance-magnitudes to the calibration zero-frequency impedance-magnitudes,
wherein the comparing the probe zero-frequency impedance-magnitudes to the calibration zero-frequency impedance-magnitudes comprises interpolating the calibration zero-frequency impedance-magnitudes, so as to produce one or more interpolated zero-frequency calibration impedance-magnitudes that best match the one or more probe zero-frequency impedance-magnitudes,
wherein the one or more first impedance-magnitudes and the one or more second impedance-magnitudes are derived by applying voltage gradients between pairs of body-surface electrodes of the one or more body-surface electrodes, and measuring, using probe electrodes, voltages induced at the organ,
wherein the method comprises a calibration phase and a tracking phase,
wherein the calibration phase comprises,
a location measurement step, in which a position tracking system accurately measures a location in the organ,
in parallel, an impedance acquisition step, in which, the position tracking system measures, at the location in the organ, respective calibration impedance-magnitudes at two frequencies,
an impedance derivation step, in which, based on the calibration impedance-magnitudes, a processor derives multiple respective zero-frequency calibration-impedances $\{Z_{Cal}(0)\}$,
an impedance calibration step, in which the processor correlates the derived multiple zero-frequency calibration-impedances with the respective location,
a storing step, in which the processor stores in a memory the multiple zero-frequency calibration-impedances with corresponding coordinates of the measured locations, wherein the process repeats itself over the various calibrated locations, until a portion of the organ is location-calibrated,
wherein, during the tracking phase, several probes are present in the organ and hence lower the impedances measured by probe,
wherein the tracking phase comprises,
a probe impedance-magnitude measurement step, in which lowered or deviating impedances, resulting from several probes being present in the organ, are again measured at two different frequencies,
a derivation step, in which the processor derives, from the measured probe impedance-magnitudes, zero-frequency probe-impedances, $\{Z_{PT}(0)\}$,
a location retrieval step, in which the processor finds in the calibration phase results a location having best-correlated zero-frequency impedances with those of a given unknown location, wherein the processor correlates the zero-frequency probe-impedances with the zero-frequency calibration-impedances that were stored in the memory at the storing step of the calibration phase, to find zero-frequency calibration-impedances, $\{Z_{Cal}*(0)\}$, that are best correlated with zero-frequency probe impedances $\{Z_{PT}(0)\}$, and then retrieving the measured location that corresponds to the zero-frequency calibration-impedances $\{Z_{Cal}*(0)\}$, and
a location indicating step, in which the processor estimates the unknown given based on the calibration results, wherein, the zero-frequency calibration-impedances $\{Z_{Cal}*(0)\}$ is a result of interpolation between values included in a set zero-frequency calibration-impedance locations $\{Z_{Cal}(0)\}_{Locations}$, and the processor calculates a corresponding interpolated location between the measured locations, and wherein the processor indicates the location of the probe that was estimated on a display.

2. The method according to claim 1, wherein the steps of measuring one or more first impedance-magnitudes and measuring one or more second impedance-magnitudes are performed in parallel with the steps of estimating one or more probe zero-frequency impedance-magnitudes between the probe and the one or more body-surface electrodes and estimating the location of the probe in the organ based on the one or more probe zero-frequency impedance-magnitudes.

3. The method according to claim 1, wherein the first electrical frequency and the second electrical frequency are applied simultaneously.

4. A location tracking method, comprising:
measuring one or more first impedance-magnitudes, between a probe located at a location in an organ of a patient and one or more body-surface electrodes, at a first electrical frequency;
measuring one or more second impedance-magnitudes, between the probe located at the location and the one or more body-surface electrodes, at a second electrical frequency;
estimating, based on the measured first and second impedance-magnitudes, one or more probe zero-frequency impedance-magnitudes between the probe and the one or more body-surface electrodes; and
estimating the location of the probe in the organ based on the one or more probe zero-frequency impedance-magnitudes,
wherein the estimating the one or more probe zero-frequency impedance-magnitudes comprises reducing a capacitive distortion in the first and second impedance-magnitudes that were measured at the first and second electrical frequencies, and
wherein the capacitive distortion is caused by at least another probe located in the organ,
wherein the one or more first impedance-magnitudes and the one or more second impedance-magnitudes are derived by applying voltage gradients between pairs of body-surface electrodes of the one or more body-surface electrodes, and measuring, using probe electrodes, voltages induced at the organ,
wherein the method comprises a calibration phase and a tracking phase,
wherein the calibration phase comprises,
a location measurement step, in which a position tracking system accurately measures a location in the organ,
in parallel, an impedance acquisition step, in which, the position tracking system measures, at the location in the organ, respective calibration impedance-magnitudes at two frequencies,
an impedance derivation step, in which, based on the calibration impedance-magnitudes, a processor derives multiple respective zero-frequency calibration-impedances $\{Z_{Cal}(0)\}$,
an impedance calibration step, in which the processor correlates the derived multiple zero-frequency calibration-impedances with the respective location,
a storing step, in which the processor stores in a memory the multiple zero-frequency calibration-impedances with corresponding coordinates of the measured locations, wherein the process repeats itself over the various calibrated locations, until a portion of the organ is location-calibrated,
wherein, during the tracking phase, several probes are present in the organ and hence lower the impedances measured by probe,
wherein the tracking phase comprises,
a probe impedance-magnitude measurement step, in which lowered or deviating impedances, resulting from several probes being present in the organ, are again measured at two different frequencies,
a derivation step, in which the processor derives, from the measured probe impedance-magnitudes, zero-frequency probe-impedances, $\{Z_{PT}(0)\}$,
a location retrieval step, in which the processor finds in the calibration phase results a location having best-correlated zero-frequency impedances with those of a given unknown location, wherein the processor correlates the zero-frequency probe-impedances with the zero-frequency calibration-impedances that were stored in the memory at the storing step of the calibration phase, to find zero-frequency calibration-impedances, $\{Z_{Cal}*(0)\}$, that are best correlated with zero-frequency probe impedances $\{Z_{PT}(0)\}$, and then retrieving the measured location that corresponds to the zero-frequency calibration-impedances $\{Z_{Cal}*(0)\}$, and
a location indicating step, in which the processor estimates the unknown given based on the calibration results, wherein, the zero-frequency calibration-impedances $\{Z_{Cal}*(0)\}$ is a result of interpolation between values included in a set zero-frequency calibration-impedance locations $\{Z_{Cal}(0)\}_{Locations}$, and the processor calculates a corresponding interpolated location between the measured locations, and wherein the processor indicates the location of the probe that was estimated on a display.

* * * * *